US006166289A

United States Patent [19]
Harris et al.

[11] Patent Number: 6,166,289
[45] Date of Patent: Dec. 26, 2000

[54] IRAK MODIFIED TRANSGENIC ANIMALS

[75] Inventors: Crafford A. Harris, Easton, Pa.; John J. Siekierka, Towaco; Per A. Peterson, Bedminster, both of N.J.; Wai-Ping Leung, San Diego, Calif.

[73] Assignee: Ortho-McNeil Pharmacueticals, Raritan, N.J.

[21] Appl. No.: 09/311,509

[22] Filed: May 13, 1999

Related U.S. Application Data

[60] Provisional application No. 60/085,570, May 15, 1998.

[51] Int. Cl.$^7$ .......................... A01K 67/027; C12N 15/00
[52] U.S. Cl. ............................. 800/18; 800/14; 800/21; 800/25
[58] Field of Search .................................. 800/8, 14, 18, 800/21, 22, 25; 435/325

[56] References Cited

FOREIGN PATENT DOCUMENTS

WO 96/17926   6/1996   WIPO .

OTHER PUBLICATIONS

Palmiter et al. Science, vol. 222, p. 809–814, Nov. 1983.
Pursel et al., J. Reprod. Fert. Suppl. vol. 40, p. 235–245, 1990.
Wu et al., "New Strategies for Gene Knockout" in Methods in Gene Technology, CRC press, Inc. Boca Raton, Florida USA, p. 339–365, May 3, 1997.
Trofimova et al., Journal of Biological Chemistry, vol. 271 (30), p. 17609–17612, 1996.
Centanni et al., Mammalian Genome, vol. 9, p. 340–341, Apr. 1998.
Akira, Shizuo; Kishimoto, Tadamitsu. IL–6 and NF–IL6 in Acute–Phase Response and Viral Infection. Immunological Reviews. No. 127, 1992.
Baldwin Jr., Alberts S. The NF– B and I B Proteins: New discoveries and Insights. Annu. Rev. Immunol., 14:649–81, 1996.
Bankers–Fulbright, Jennifer L.; Kalli, Kimberly R.; McKean, David J. Interleukin–1 Signal Transduction. Life Sciences, vol. 59, No. 2, pp. 61–83, 1996.
Belvin, Marcia P.; Anderson, Kathryn V. A Conserved Signaling Pathway: The Drosophila Toll–Dorsal Pathway. Annu. Rev. Cell Biol, 12:393–416, 1996.
Bird, Timothy A.; Kyriakis, John M.; Tyshler, Leanna; Gayle, Margit; Milne, Alison; Virca, G. Duke. Interleukin–1 Activates p54 Mitogen–activated Protein (MAP) Kinase/ Stress–activated Protein Kinase by a Pathway That Is Independent of p21$^{ras}$, Raf–1, and MAP Kinase Kinase. The Journal of Biological Chemistry, vol. 269, No. 50, Issue of Dec. 16, pp. 31836–31844, 1994.
Cao, Zhaodan; Henzel, William J.; Gao, Xiong. IRAK: A Kinase Associated with the Interleukin–1 Receptor. Science, vol. 271, Feb. 23, 1996.
Cao, Zhadon; Xiong, Jessie; Takeuchi, Masahiro; Kurama, Takeshi; Goeddel, David V. TRAF6 is a signal transducer for interleukin–1. Letters To Nature, vol. 383, Oct. 3, 1996.

Centanni, John M.; de Miguel, Maria; Gopalan, Ganesan; Gilbert, Debra J.; Copeland, Neal G.; Jenkins, Nancy A.; Donovan, Peter J. Interleukin–1 receptor–associated kinase gene Illrak maps to the mouse X Chromosome. Mammalian Genome 9, Brief Data Reports, pp. 340–341.
Croston, Glenn E.; Cao, Zhaodan, Goeddel, David V. NF–κB Activation by Interleukin–1 (IL–1) Requires an IL–1 Receptor–associated Protein Kinase Activity. The Journal of Biological Chemistry, vol. 270, No. 28, Issue of Jul. 14, pp. 16514–16517, 1995.
Didonato, Joseph A.; Hayakawa, Makio; Rothwarf, David M.; Zandi, Ebrahim; Karin, Michael. A cytokine–responsive IκB kinase that activates the transcription factor NF–κB. Nature, 388, 548–554, 1997.
Dinarello, Charles A.; Biologic Basis for Interleukin–1 in Disease. The Journal of The American Society of Hematology, vol. 87, No. 6, Mar. 15, 1996.
Fung–Leung, Wai–Ping; Schilham, Marco W.; Rahemtulla, Amin; Kundig, Thomas M.; Vollenwieder, Maja; Potter, Julia; van Ewijk, Willem; Mak, Tak W. Cell, vol. 65, 443–449, May 3, 1991.
Glaccum, Moira B.; Stocking, Kim L.; Charrier, Keith; Smith, Jeffrey L.; Willis, Cindy R.; Maliszewski, Charles; Livingston, David J.; Peschon, Jacques J.; Morrissey, Philip J. Phenotypic and Functional Characterization of Mice That Lack the Type I Receptor for IL–1. The Journal of Immunology, 159:3364–3371, 1997.
Huang, Jianing; Gao, Xiong; Li, Shyun; Cao, Zhaodan. Recruitment of IRAK to the interleukin 1 receptor complex requires interleukin 1 receptor accessory protein. Pro. Natl. Acad. Sci. USA, vol. 94, pp. 12829–12832, Nov. 1997.
Kanakaraj, Palanisamy; Duckworth, Brian; Azzoni, Livio; Kamoun, Malek; Cantley, Lewis C.; Perussia, Bice. J. Exp. Med., vol. 179, 551–558, Feb. 1994.
Korherr, Christian; Hofmeister, Robert; Wesche, Holger; Falk, Werner. A critical role for interleukin–1 receptor accessory protein in interleukin–1 signaling. Eur. J. Immunol., 27:262–267, 1997.
Labow, Mark; Shuster, David; Zetterstrom, Maria; Nunes, Perla; Terry, Robert; Cullinan, Emily B.; Bartfai, Tamas; Solorzano, Carmen; Moldawer, Lyle L.; Chizzonite, Richard; McIntyre, Kim W. Absence of IL–1 Signaling and Reduced Inflammatory Response in IL–1 Type I Receptor–Deficient Mice. The Journal of Immunology, 159:2452–2461, 1997.
Lemaitre, Bruno; Nicholas, Emmanuelle; Michaut, Lydia; Reichhart, Jean–Marc; Hoffman, Jules A. The Dorsoventral Regulatory Gene Cassette spatzle/Toll/cactus Controls the Potent Antifungal Response in Drosophila Adults. Cell, vol. 86, 973–983, Sep. 20, 1996.

(List continued on next page.)

*Primary Examiner*—Deborah J. R. Clark
*Assistant Examiner*—Shin-Lin Chen
*Attorney, Agent, or Firm*—John W. Wallen

[57] ABSTRACT

A transgenic animal with alterations in an IRAK gene is prepared by introduction of an altered IRAK gene into a host animal. The resulting transgenic animals do not produce functional IRAK molecules. Cells and cell lines derived from these animals also contain the altered IRAK gene.

6 Claims, 10 Drawing Sheets

OTHER PUBLICATIONS

Leon, Lisa R.; Conn, Carole A.; Glaccum, Moira; Kluger, Matthew J. IL–1 type I receptor mediates acute phase response to turpentine but not lipopolysaccharide, in mice. The American Physiological Society, 1996.

Malinin, Nikolal L.; Boldin, Mark P.; Kovalenko, Andrel V.; Wallach, David. MAP3K–related kinase Involved in NF–κB Induction by TNF, CD95 and IL–1. Letters to Nature, vol. 385, Feb. 6, 1997.

Mercurio, Frank; Zhu, Hengyi; Murray, Brion W.; Shevchenko, Andrej; Bennett, Brydon L.; Li, Jian wu; Young, David B.; Barbosa, Miguel; Mann, Matthias. IKK–1 And IKK–2; Cytokine–Activated IκB Kinases Essential for NF–κB Activation. Science, vol. 278, Oct. 31, 1997.

Muzio, Marta; Ni, Jian; Feng, Ping; Dixit, Vishva M. IRAK (Pelle) Family Member IRAK–2 and MyD88 as Proximal Mediators of IL–1 Signaling. Science, vol. 278, Nov. 28, 1997.

Natoli, Gioacchino; Costanzo, Antonio; Moretti, Francesca; Fulco, Marcella; Balsano, Clara; Levrero, Massimo. Tumor Necrosis Factor (TNF) Receptor 1 Signaling Downstream of TNF Receptor–associated Factor 2. The Journal of Biological Chemistry, vol. 272, No. 42, Issue of Oct. 17, pp. 26079–26082, 1997.

Osborn, Laurelee; Kunkel, Steven; Nabel, Gary J. Tumor necrosis factor α and interleukin 1 stimulate the human immunodeficiency virus enhancer by activation of the nuclear factor κB. Proc. Natl. Acad. Sci. USA, vol. 86, pp. 2336–2340, Apr. 1989.

Pulverer, Bernd J.; Kyriakis, John M.; Avruch, Joseph; Nikolakaki, Eleni; Woodgett, James R. Phosphorylation of c–jun mediated by MAP kinases. Letters to Nature, vol. 353, Oct. 17, 1991.

Raingeaud, Joel; Gupta, Shashi; Rogers, Jeffrey S.; Dickens, Martin; Han, Jiahuai; Ulevitch, Richard J.; Davis, Roger J. Pro–inflammatory Cytokines and Environmental Stress Cause p38. Mitogen–activated Protein Kinase Activation by Dual Phosphorylation on Tyrosine and Threonine. The Journal of Biological Chemistry, vol. 270, No. 13, Issue of Mar. 31, pp. 7420–7426, 1995.

Ridley, Simon H.; Sarsfield, Simon J.; Lee, John C.; Bigg, Heather F.; Cawston, Tim E.; Taylor, David J.; DeWitt, David L.; Saklatvala, Jeremy. Actions of IL–1 are Selectively Controlled by p38 Mitogen–Activated Protein Kinase. The Journal of Immunology, 158:3165–3173, 1997.

Shelton, Christopher A.; Wasserman, Steven A. pelle Encodes a Protein Kinase Required to Establish Dorsoventral Polarity in the Drosophila Embryo. Cell, vol. 72, 515–525, Feb. 26, 1993.

Song, Ho Yeong; Regnier, Catherine H.; Kirshning, Carsten J.; Goeddel, David V.; Rothe, Mike. Tumor necrosis factor (TNF)–mediated kinase cascades; Bifurcation of Nuclear Factor–κB and c–jun N–terminal kinase (JNK/SAPK) pathways as TNF receptor–associated factor 2. Proc. Natl. Acad. Sci. USA, vol. 94, pp. 9792–9796, Sep. 1997.

Su, Bing; Karin, Michael. Mitogen–activated protein kinase cascades and regulation of gene expression. Current Opinion in Immunology. 8:402–411, 1996.

Trofimova, Marina; Sprenkle, Amy B.; Green, Melissa; Sturgill, Thomas W.; Goebl, Mark G.; Harrington, Maureen A. Developmental and Tissue–specific Expression of Mouse Pelle–like Protein Kinase. The Journal of Biological Chemistry, vol. 271, No. 30, Issue of July 26, pp. 17609–17612, 1996.

Trotta, Rosanna; Kanakaraj, Palanisamy; Perussia, Bice. FcγR–dependent Mitogen–activated Protein Kinase Activation in Leukocytes: A Common Signal Transduction Event Necessary for Expression of TNF–α and Early Activation Genes. J. Exp. Med., vol. 184, Sep. 1996.

Wesche, Holger; Korherr, Christian; Kracht, Michael; Falk, Werner; Resch, Klaus; Martin, Michael U. The Interleukin–1 Receptor Accessory Protein (IL–1RAcP) Is Essential for IL–1–induced Activation of Interleukin–1 Receptor–associated Kinase (IRAK) and Stress–activated Protein Kinases (SAP Kinases). The Journal of Biological Chemistry, vol. 272, No. 12, Issue of Mar. 21, pp. 7727–7731, 1997.

Westwick, John K.; Wietzel, Christoff; Minden, Audrey; Karin, Michael; Brenner, David A. Tumor Necrosis Factor α Stimulates AP–1 Activity through Prolonged Activation of the c–Jun Kinase. The Journal of Biological Chemistry, vol. 269, No. 42, Issue of Oct. 21, pp. 26396–26401, 1994.

Woronicz, John D.; Gao, Xiong; Cao, Zhaodan; Rothe, Mike; Goeddel, David V. IκB Kinase–β: NF–κB Activation and Complex Formation with IκB Kinase–α and NIK. Science, vol. 278, Oct. 31, 1997.

Vanden, Berghe, Wim; Plaisance, Stephane; Boone, Elke; De Bosscher, Karolien; Schmitz, M. Lienhard; Fiers, Walter; Haegeman, Guy. p38 and Extracellular Signal–regulated Kinase Mitogen–activated Protein Kinase Pathways Are Required for Nuclear Factor–κB p65 Transactivation Mediated by Tumor Necrosis Factor. The Journal of Biological Chemistry, vol. 273, Issue of Feb. 6, pp. 3285–3290, 1998.

Zheng, Hui; Fletcher, Daniel; Kozak, Wieslaw; Jiang, Minghao; Hofmann, Kathryn J.; Conn, Carole A.; Soszynski, Dariusz; Grabiec, Christina; Trumbauer, Myrna E.; Shaw, Alan; Kostura, Matthew J.; Stevens, Karla; Rosen, Hugh; North, Robert J.; Chen, Howard Y.; Tocci, Michael J.; Kluger, Matthew J.; Van der Ploeg, Lex H.T. Resistance to Fever Induction and Impaired Acute–Phase Response in Interleukin–1β–Deficient Mice. Immunity, vol. 3, 9–19, Jul. 1995.

IRAK MODIFIED TRANSGENIC ANIMALS

This application claims the benefit of U.S. provisional application No. 60/085,570 filed May 15, 1998.

FIELD OF THE INVENTION

The present invention relates to transgenic nonhuman animals wherein an IL-1 receptor associated serine/threonine kinase (IRAK) gene is altered, producing an animal lacking functional IRAK protein.

BACKGROUND OF THE INVENTION

Interleukin-1 (IL-1α and IL-1β) plays an important role in inflammation, acting locally and systemically to induce other proinflammatory cytokines, chemotactic factors, adhesion molecules, acute phase proteins, and fever (1). Animals which lack expression of IL-1 or IL-1 receptor have reduced inflammatory responses (2–5). Cellular responses to IL-1 are mediated by a cascade of intracellular signaling events including activation of the stress-activated MAP kinases, c-Jun N-terminal kinase (JNK) and p38, as well as transcription factors NF-κB (6). Upon IL-1 binding, IL-1 receptor type I forms a complex with IL-1 receptor accessory protein (IL-1R AcP) (7–9). IL-1 receptor associated serine/threonine kinase (IRAK), and a recently identified homologue IRAK-2, are rapidly recruited to this receptor complex via the adaptor protein MyD88 (10–13). IRAK becomes phosphorylated and subsequently interacts with TRAF6, a member of the TNF receptor associated factor (TRAF) family (13,14). TRAF6 has been implicated in activation of both JNK and NF-kB (14, 15). TRAF6 associates with NF-κB inducing kinase (NIK), a MAP 3 kinase related protein which is essential for TNFα and IL-1 mediated NF-κB activation but has no effect on the activation of JNK or p38 (15–17). NIK interacts with and may directly activate the recently identified IκB kinases (18–20). IκB kinases are responsible for activation of NF-κB via phosphorylation of its inhibitory partners, the IκB proteins, leading to their degradation by proteasomes (21).

IRAK and IRAK-2 are homologous to Pelle, a Drosophila protein kinase identified genetically to be important in dorsal-ventral pattern formation and in pathogen resistance (22, 23). Pelle is essential for the activation of Dorsal, an NF-κB like protein which is mediated by Toll, an IL-1 receptor homologue in Drosophila (24). The rapid IL-1 dependent association of IRAK and IRAK-2 with the IL-1 receptor complex and their homology to Pelle suggest that IRAK and/or IRAK-2 may serve important functions in initiating IL-1 signaling. However, the roles of IRAK and IRAK-2 in activation of the multiple downstream IL-1 signaling pathways have not previously been determined.

To dissect the role of IRAK in IL-1 signaling pathways, the IRAK gene was disrupted by homologous recombination and IRAK deficient fibroblasts were prepared. IL-1-induced activation of JNK, p38 and transcription factor NF-κB, and subsequent induction of IL-6 were analyzed in the IRAK-deficient cells.

SUMMARY OF THE INVENTION

To understand the functional role of IRAK in different cell types, mice that do not express the functional IRAK were generated by homologous recombination (HR) in embryonic stem (ES) cells and are disclosed herein. Cell lines that are derived from these mice are also disclosed herein. These mice, including the cell lines derived from them, provide a valuable animal model and tools to understand the function of IRAK and to evaluate the therapeutic effects of drugs that modulate the function or the expression of IRAK equivalents in human cells.

DETAILED DESCRIPTION OF THE INVENTION

Figure 1A:
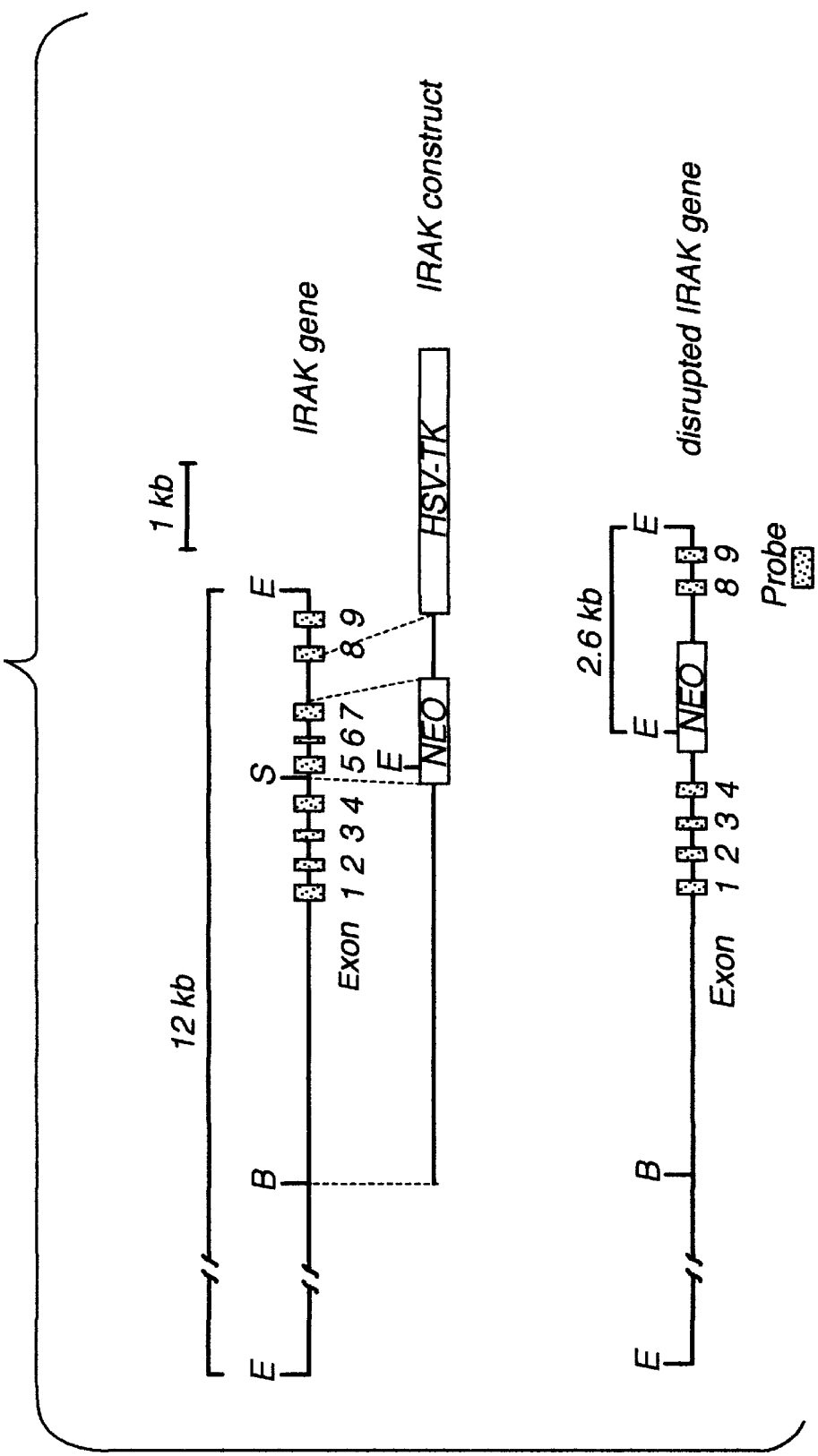
FIG. 1 Panels A–D show disruption of the mouse IRAK gene. (A) Map of the mouse IRAK gene and construct. A genomic DNA fragment containing the 5' portion of the mouse IRAK gene was used as the homologous region for recombination. Exon 5 to exon 7 of the gene was replaced by a neomycin resistant gene cassette (NEO). A herpes simplex-thymidine kinase gene (HSV-TK) was placed 3' of the construct. Restriction sites are BamHI (B), EcoRI (E) and SpeI (S). (B) Disruption of the single IRAK allele in male embryonic stem cells. Genomic DNAs from embryonic stem cells with the wild-type (+) or disrupted (−) IRAK gene were digested with EcoRI and hybridized to the DNA probe shown in (A). The 12 kb DNA band of the wild type allele and the 2.6 kb band of the disrupted allele detected in hybridization are also shown in (A). (C) Absence of IRAK protein in IRAK-deficient cells. Primary embryonic EF cells were prepared as described in the Materials and Methods. Proteins from control (+) and IRAK-deficient (−) EF cells were separated by 10% SDS-PAGE and IRAK was detected by immunoblotting using an IRAK-specific antibody. Equal loading of proteins was demonstrated by subsequent blotting with an antibody to ERK-2. (D) The Southern blot DNA patterns of IRAK wild type, heterozygous, and homozygous knockout mice are shown.

The IRAK knockout mice that were generated in the present invention provide a model in which the IRAK gene was disrupted by homologous recombination (HR). The process of generating the knockout mice can be divided into 4 basic stages:

1. cloning of the IRAK gene and preparation of DNA construct for transfection of embryonic stem (ES) cells;
2. isolating ES cells in which the IRAK gene has been disrupted by HR;
3. generating chimeric mice from mouse embryos injected with the knockout ES cells; and
4. breeding chimeric mice to obtain knockout mice through germline transmission.

The present invention utilizes a cloned genomic DNA encoding the IRAK protein and describes the cloning and characterization of the mouse IRAK gene. Transgenic animals are generated which have altered the IRAK gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with IRAK-mediated responses. A transgenic animal carrying a "knockout" of IRAK is useful for the establishment of a nonhuman model for diseases involving IRAK equivalents in the human.

A transgenic mouse carrying the disrupted IRAK gene was generated by homologous recombination of a target DNA construct with the endogenous gene in the chromosome. The DNA construct was prepared from a genomic clone of IRAK which was isolated from a genomic DNA library.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered IRAK gene generally should not fully encode the same IRAK as native to the host animal, and its expression product should be altered to a minor or great degree, or absent altogether. However, it is conceivable that a more modestly modified IRAK gene will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)]. Transgenes can be efficiently introduced into the ES cells by standard techniques such as DNA transfection or by retrovirusmediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since IRAK is an independent component of a complex mechanism, the proteins, including that encoded by IRAK DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as IRAK) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene flanking the DNA construct. Cells with nonhomologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germline of a non-human animal by way of human intervention, including but not limited to, the methods described herein. The targeted genes of the invention include DNA sequences which are designed to specifically alter cognate endogenouos genes.

All the above applications have to be verified in animal tests and eventually clinical trials. One approach to determine the functional role of the drug target is to study the defects resulting from the disrupted gene in a whole animal. The IRAK knockout mice that have been generated and are disclosed herein will allow the definition of the function of IRAK which is critical in deciding the types of modulators are most suitable in therapies.

Any IRAK function that is detected in the knockout mice of the present invention would provide evidence of the existence of alternative novel IRAK subtypes which may then be isolated from the knockout mice of the present invention.

The absence of functional IRAK in the knockout mice of the present invention are confirmed, for example, in RNA analysis, protein expression detection, receptor binding assays, enzymatic activity assays, and other IRAK functional studies. For RNA analysis, RNA samples are prepared from different organs of the knockout mice and the IRAK transcript are detected in Northern blots using oligonucleotide probes specific for the transcript.

Polyserum and monoclonal antibodies that are specific for the mouse IRAK are produced. The absence of intact IRAK in the knockout mice are studied, for example, in flow cytometric analysis, in immunohistochemical staining, and in receptor binding and/or enzymatic activity assays using IRAK-specific antibodies. Alternatively, functional assays are performed using preparations of different cell types collected from the knockout mice.

IL-1 is a proinflammatory cytokine with pleiotropic effects in inflammation. IL-1 binding to its receptor triggers a cascade of signaling events, including activation of the stress-activated MAP kinases, c-Jun N-terminal kinase (JNK) and p38 MAP kinase, as well as transcription factor NF-κB. IL-1 signaling results in cellular responses through induction of inflammatory gene products such as IL-6. One of the earliest events in IL-1 signaling is the rapid interaction of IL-1 receptor associated kinases, IRAK and IRAK-2, with the receptor complex. The relative roles of IRAK and IRAK-2 in IL-1 signaling pathways and subsequent cellular responses have not been previously determined. To evaluate the importance of IRAK in IL-1 signaling, IRAK deficient mouse fibroblasts cells were prepared and studied.

The present invention demonstrates that IRAK plays an important role in activating multiple IL-1 signaling pathways that lead to the induction of IL-1-responsive gene products such as IL-6. In the absence of IRAK, induction of JNK and p38 activities was significantly reduced at all concentrations of IL-1 tested, although not completely eliminated. The present invention shows that IRAK is required for optimal induction of JNK and p38 kinases and that loss of its function cannot be completely compensated by IRAK-2 or other related kinases. Activation of JNK and p38 have been reported to be mediated by cascades of upstream kinases including MAP 2-, MAP 3- and MAP 4-kinases (29). At which levels within these cascades IRAK may act to induce JNK and p38 activity remains to be determined.

In contrast to the effects on JNK and p38, defects in NF-κB activation in IRAK-deficient cells could be overcome by high concentrations of IL-1. Related kinases such as IRAK-2 may be able to fully activate the NF-κB pathway under these conditions. However, induction of cellular response to IL-1, such as IL-6 production, is dramatically reduced in IRAK-deficient cells even at high IL-1 concentrations. This suggests that activation of NF-κB alone is not sufficient for optimal induction of IL-1 mediated cellular responses. Induction of IL-6 and other IL-1 responsive gene products may be mediated synergistically by multiple pathways, including IKK/IKB-dependent activation of NF-κB, and JNK/p38-mediated pathways. In the case of IL-6 secretion, the dramatic decrease in its induction by IL-1 in IRAK-deficient cells, even in the presence of full activation of NF-κB DNA-binding activity, may result from decreased activation of JNK and p38-dependent signaling pathways. This possibility is supported by a recent report that p38 and other MAP kinases are involved in TNF-induced IL-6 gene expression via modulation of transactivation potential of NF-kB without affecting its DNA binding activity (37).

The observation disclosed herein of significant reduction in multiple signaling pathways and in IL-6 production induced by IL-1 in IRAK-deficient cells suggests that modulators of IRAK or IRAK-related kinases may be therapeutically useful for the treatment of IL-1-mediated inflammatory diseases.

The genetically modified animals of the present invention show that IL-1-mediated activation of JNK, p38 and NF-κB were all reduced in embryonic fibroblasts deficient in IRAK expression. In addition, IL-6 production in response to IL-1 was also dramatically reduced in IRAK deficient embryonic fibroblasts and in skin fibroblasts prepared from IRAK deficient mice. These results demonstrate that IRAK plays an essential proximal role in coordinating multiple IL-1 signaling pathways for optimal induction of cellular responses.

The following Examples are presented for the purpose of illustrating the present invention and are not to be construed as a limitation on the scope of this invention.

EXAMPLE 1

Gene Targeting

The knockout construct was composed of 4 parts arranged in a 5' to 3' order: (1) A 4.5 kb BamHI-SpeI DNA fragment from a 129/Ola mouse genomic clone covering exon 1–4 and the 5' promoter region of the IRAK gene used as the long homologous region for recombination. (2) A 1.2 kb DNA cassette containing a neomycin resistant gene with its own promoter and polyadenylation signal. (3) A 1 kb DNA fragment obtained by PCR using exon 7 specific oligonucleotide (5'-CTGATCTGGCACCTTTATTGGCA-3') [SEQ.ID.NO.: 1] and exon 8 specific oligonucleotide (5'-CCAGAAGAATGTCCAGTCGTTGA-3') [SEQ.ID.NO.: 2] used as a short homologous region for recombination. (4) An HSV-thymidine kinase DNA cassette with its own promoter and polyadenylation signal. The IRAK gene, the neomycin resistant gene and the thymidine kinase gene were in the same orientation of transcription.

In this knockout construct, the mouse IRAK gene was disrupted by deleting exon 5, 6 and most of the exon 7 of the gene which encode the N-terminal portion of the kinase domain, subdomain I to V, including conserved amino acids involving in ATP binding.

Transfection of ES Cells with the IRAK DNA Construct

Embryonic stem (ES) cells E14 (Hooper et al., 1987, HPRT-deficient (Lesch-Nyhan) mouse embryos derived from germline colonization by cultured cells. Nature 326, 292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, E. J. (1987) Embryo-derived Stem Cell Lines. In: Teratocarcinomas and Embryonic Stem Cells. E. J. Robertson, ed. (Oxford, Washington D.C.: IRL Press), p 71–112.). EF were treated with 10 mg/ml mitomycin C (Sigma) in culture medium for 2 hours to stop cell division prior to the use as feeder cells.

For DNA transfection, the DNA construct was linearized by NotI digestion. DNA was then precipitated by 2 volumes of ice cold ethanol at −20° C. for 1 hour. Precipitated DNA was pelletted by centrifugation, rinsed once with 0.5 ml 70% ethanol, air dried and then dissolved at 1 mg/ml in phosphate-buffered saline (Gibco). ES cells were harvested by trypsin treatment and resuspended at $6.25 \times 10^6$ cell/ml in culture medium. DNA construct (20 μg) was added to 0.8 ml of ES cell suspension for electroporation at 250 μF and 340 Volts using the Gene Pulser (BioRad).

Transfected ES cells were plated onto EF coated 90 mm plates at $2.5 \times 10^6$/plate in culture medium. Two days later, cells were subjected to drug selection in medium containing 400 μg/ml G418 (Geneticin, Gibco) and 2 μM GANC (Cytosin, Syntex). Culture medium was changed daily. Massive cell death was obvious starting day 4 and most of the dead cells were removed through daily medium change. Surviving cell colonies were observable under microscope by day 7 and by day 10 they were visible on the plates without a microscope.

PCR Screen of Transfected ES Cells for Homologous Recombination

The size of ES colonies on day 11 after transfection was large enough for PCR screening. To collect cell colonies, culture medium in the 90 mm plates was aspirated and 10 ml PBS was added.

Individual cell colonies were located with the aid of a stereomicroscope, collected in a 20 ml volume with an autopipetteman and transferred into 96 well-plates. To prepare single cell suspension of the ES colonies, 25 μl of 0.25% trypsin (Gibco) was added per well in 96 well-plates. After 8 minutes of trypsin treatment at 37° C., 25 μl of culture medium was added. All the ES colonies were still maintained in culture as master plates while screening by PCR for homologous recombination events was performed. To prepare master plates, 60 μl of each cell sample was transferred to 96-well plates which had been coated with EF cells and contained 180 μl/well of the culture medium containing G418 and GANC.

For the first round PCR screen, each cell lysate sample was prepared from 12 cell colonies which arrayed as one row of samples in the 96 well-plates. After the preparation of master plates, the remaining cell samples of about 90 μl/well on every row of the plates were pooled. Cells were pelleted in tubes by centrifugation for 1 minute. After draining all the medium, cells were lysed by adding 30 μl distilled water and brief vortexing. Cell lysates were prepared by first heating at 95° C. for 10 minutes, cooling to room temperature and followed by an addition of 1 μl proteinase K (10 mg/ml in water) with brief vortexing, a 90 minute incubation at 50° C. for proteinase K digestion, and then 10 minutes at 95° C. for heat inactivation of proteinase K.

PCR was carried out using the 9600 GeneAmp system (Perkin Elmer). The reaction mixtures contained 5 μl cell lysate, 4 μM of each of the two oligonucleotide primers, 200 μM each of dATP, dTTP, dCTP, and dGTP, and 5 U Ampli-Taq DNA polymerase in PCR buffer (10 mM Tris-Cl, pH8.3, 50 mM KCl, 1.5 mM $MgCL_2$ and 0.001% w/v gelatin). The reaction condition was 3 cycles of 2 minutes at 94° C., 2 minutes at 60° C., and 2 minutes at 72° C., then 40 cycles of 15 seconds at 94° C., 15 seconds at 60° C., and 1 minutes at 72° C., followed by 7 minutes at 72° C.

ES cells with the targeted gene were detected by polymerase chain reaction using neomycin resistant gene-specific oligonucleotide (5'-AACGCACGGGTGTTGGGTCGTTTG-3') [SEQ.ID.NO.: 3] and IRAK intron 8-specific oligonucleotide (5'-TCCTCACCTCTTGATGTCTCCAT-3') [SEQ.ID.NO.: 4] and the size of the amplified DNA is expected to be about 1 kb. To detect the specific DNA fragment amplified by PCR, 20 μl of the PCR samples were separated according to size by 1% agarose gel electrophoresis, blotted onto Hybond-N+ nylon membranes (Amersham), and hybridized to the $P^{32}$-labelled IRAK gene-specific oligonucleotide probe (5'GGATAAGGCTGGGGCTATCCTGATGTAAAAACT GA-3') [SEQ. ID .NO.: 5]. PCR samples with a 1 Kb DNA band detected by the oligo probe were considered as putative positive groups for further screening.

ES cells in master plates after 3–4 days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 μl PBS, treating with 40 μl 0.25% trypsin for 5 minutes at 37° C., followed by adding 90 μl culture medium. Cells were then resuspended and 20 μl of the cell samples were transferred to master plates which had been coated with EF and filled with 200 μl culture medium containing G418 and GANC. The remaining cells (110 μl/well) were transferred into eppendorf tubes. Cell lysates were prepared and homologous recombination signals were amplified by PCR and detected by hybridization as described in the previous paragraphs.

Confirmation of Homologous Recombination by Genomic Southern Hybridization

Homologous recombination was confirmed by Southern hybridization. ES cells derived from the positive colonies in PCR screen were expanded in culture and DNA was extracted as described by Maniatis et al. (Maniatis, T.; Fritsch, E. F.; Sambrook, J. (1982) Molecular Cloning, Cold Spring Harbor Laboratory pp. 280–281). Genomic DNA samples of the putative knockout cell lines were digested with the restriction enzymes EcoRI, separated by 1% agarose gel electrophoresis, blotted onto Hybond-N+ nylon membranes (Amersham) and hybridized with a ~440 bp DNA fragment specific for the mouse IRAK gene. This DNA probe fragment was obtained by PCR using intron 8-specific oligonucleotide (5'-ATGGAGACATCAAGAGGTGAGGAG-3') [SEQ.ID.NO.: 6] and exon 9-specific oligonucleotide (5'-CTCATCCAGAAGCACGTTAG-3') [SEQ.ID.NO.: 7]. This DNA probe did not hybridize to the DNA constructs that were integrated randomly in the chromosome.

Figure 1B:
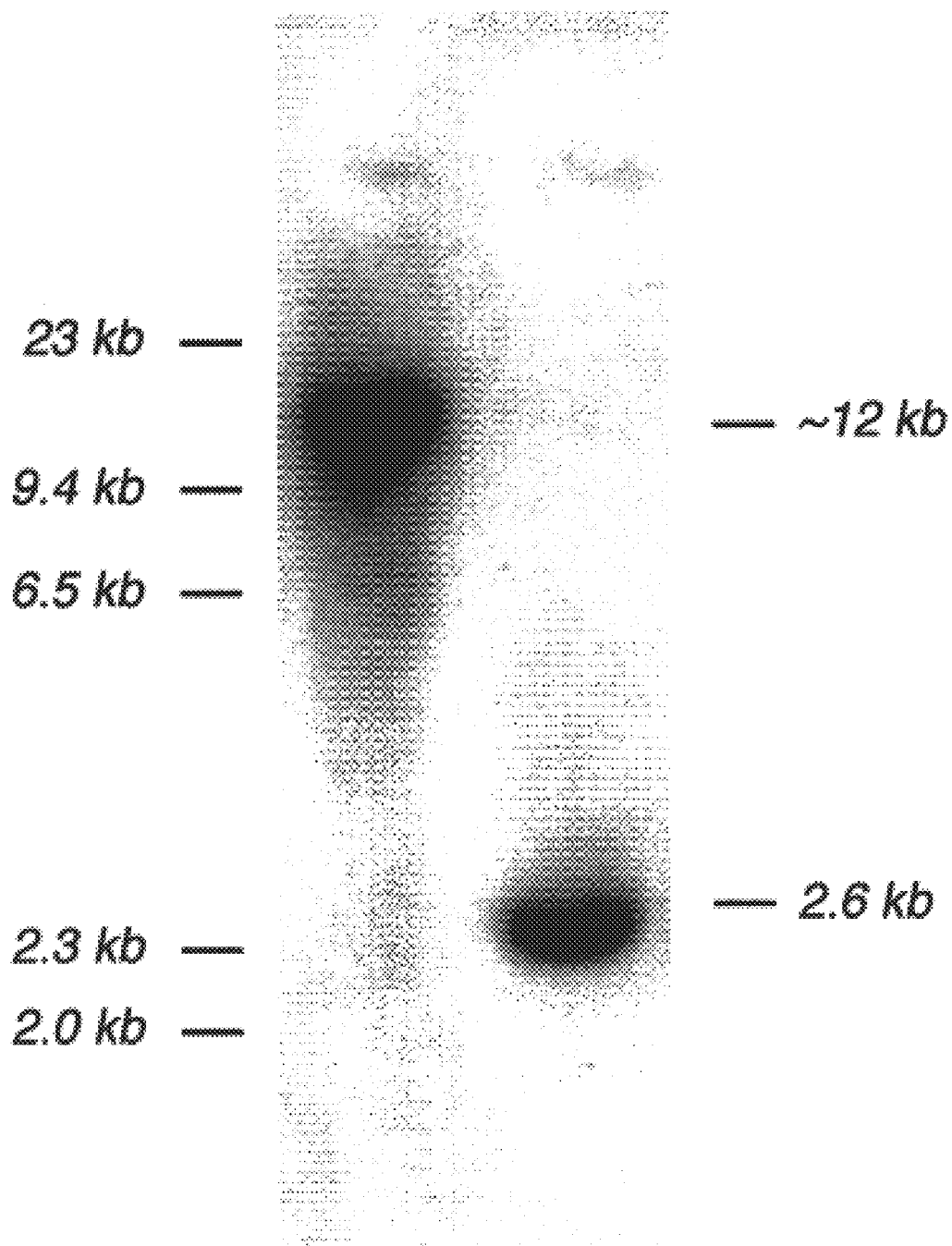

As expected from the restriction map of the mouse IRAK gene, the functional gene in parental ES cells was identified as a ~12 kb band and the disrupted gene in knockout ES cells as a 2.6 kb band resulting from an additional EcoRI site in the neomycin resistant gene (FIG. 1A). The IRAK gene was found to be located on X-chromosome by FISH analysis. The E14 ES cells were diploid cells derived from a male embryo and therefore carry only one copy of the IRAK gene. Only the functional IRAK was detected in the parental ES cells and only the disrupted IRAK gene was found in knockout ES cells (FIG. 1B).

Generation of Chimeric Mice by Embryo Injection

Mouse embryos at 3.5 day gestation stage were collected from the uteri of super-ovulated C57BL/6J mice. About 10–15 ES cells were injected into the blastocoel cavity of the embryos. Injected embryos were transferred into the uteri of pseudo-pregnant CD1 mice at 2.5 day gestation. Mice developed from these embryos were born 17 days later. Since the ES cells used were derived from the 129 Ola mouse strain with the dominant agouti coat color genes, chimeric mice were identified by the agouti coat color from ES derived cells, versus the black color from C57BL/6J mouse embryos.

ES Germline Mice Obtained by Chimeric Mouse Breeding

Chimeric mice were bred with C57BL/6J mice. These crosses are performed to test for the germline transmission of ES cells. Some of the progeny from the breeding are expected to be agouti if the chimeric male had germ line cells derived from ES cells which carry the dominant agouti coat color genes. The disrupted IRAK gene in mice was detected by genomic hybridization as described in the previous section. Genomic DNA is purified from about 1 cm of tail from each agouti mouse after weaning. The genomic DNA is isolated as described (Laird et al., supra), followed by phenol and plienol:chloroform extractions and ethanol precipitation. Genomic DNAs are digested with EcoRI, and hybridized with the 3'flanking DNA specific for the IRAK gene as described earlier. Since the IRAK gene is X-chromosome linked, all the female germline agouti mice are heterozygous for the disrupted IRAK gene.

Figure 1C:
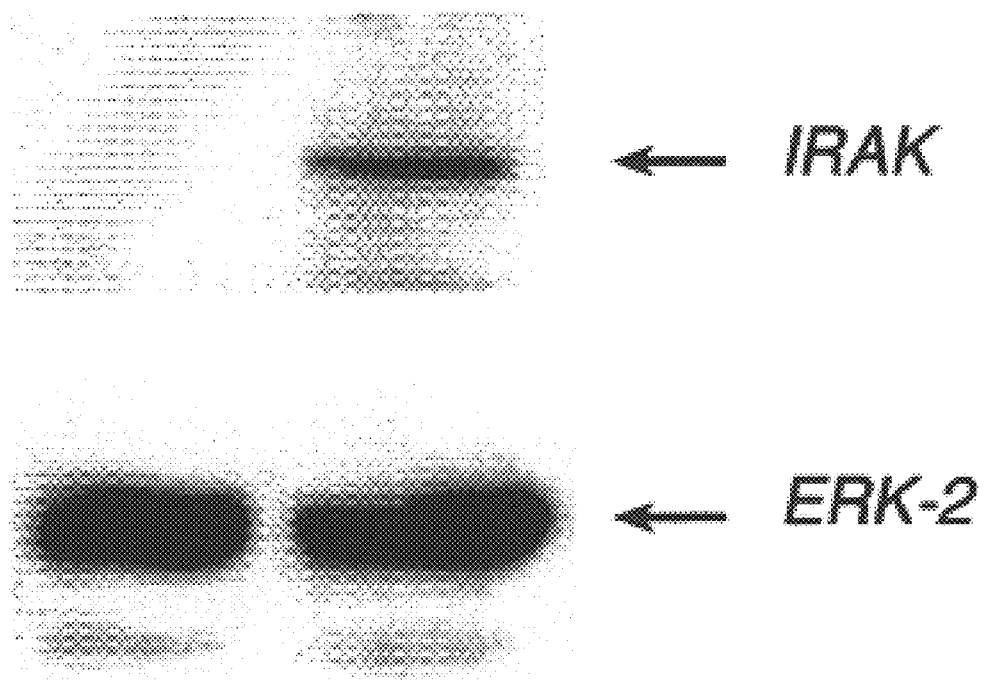
Figure 1D:
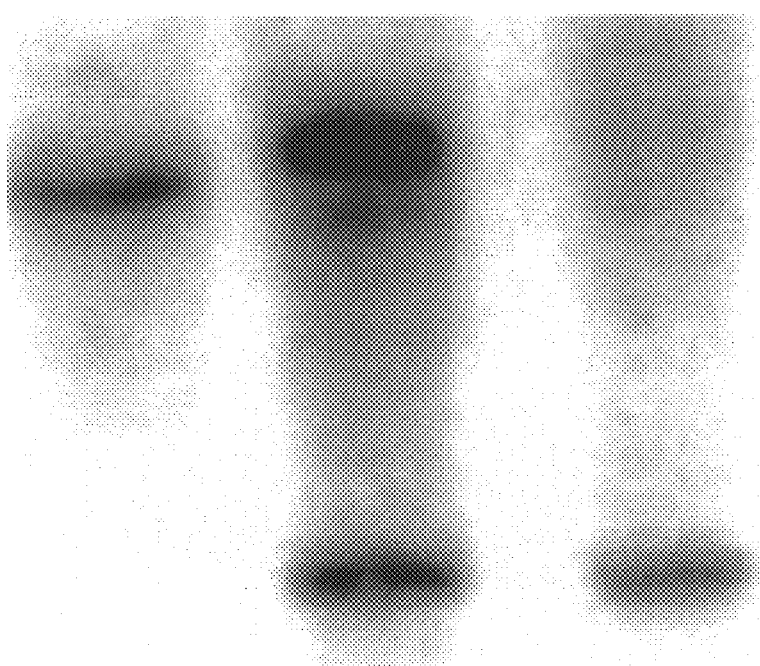

Generation of Homozygous Knockout Mice from Breeding of Hetrozygous Knockout Mice Female heterozygous knockout mice were mated with C57BL/6J mice or wild-type male littermates. It is expected that half of the male pups carry only the disrupted gene and half of the female pups are heterozygous for the disrupted gene. Surviving offspring were genotyped by Southern hybridization as described above. Homozygous female mice were obtained by further breeding of heterozygous females with knockout males. DNA patterns of wild-type, heterozygous and knockout mice are shown in FIG. 1D.

EXAMPLE 2

Characterization of IRAK Knockout Mice and Cells Derived From the Mice

Preparation of IRAK Antibody.

Polyclonal rabbit antiserum to IRAK was raised against a peptide (Bio-Synthesis, Inc., Lewisville, Tex.) corresponding to the C-terminal amino acids (657–677) of mouse IRAK protein (25).

Preparation of Embryonic Fibroblasts (EF) and Skin Fibroblasts (SF).

To prepare embryonic fibroblasts, embryonic stem cells with the disrupted IRAK gene were injected into C57BL/6J blastocysts and transferred to pseudo-pregnant mice. Embryos at day 15 gestation were harvested. Fibroblast cell suspensions were prepared by trypsin treatment of the minced embryonic tissues. Fibroblasts derived from embryonic stem cells were enriched by culturing in DMEM with 10% fetal calf serum and 1 mg/ml G418. Fibroblasts after 3–4 weeks of culture with G418 were used in the studies. Control EF cells with the wild-type IRAK gene were prepared from embryos of CD8 deficient mice (26). To prepare skin fibroblasts, mouse body skin was shaved, cut into small pieces and then subjected to trypsin treatment. Skin fibroblasts in cell suspensions were cultured in DMEM with 10% fetal calf serum.

Cell Stimulation.

Control and IRAK-deficient cells ($9 \times 10^5$/plate) were plated overnight in 100 mm cell culture plates with DMEM containing 5% fetal calf serum. EF cells were kept in presence of 200 μ/ml G418. Before each experiment, cells were starved in serum-free DMEM for 4 hours. The cells were then stimulated with IL-1 β (R&D Systems, Minneapolis, Minn.) or TNF-α (Genzyme, Cambridge, Mass.) at 37° C. After stimulation, cells were scraped from the plates in ice-cold PBS and used immediately.

In vitro kinase assay. After stimulation, cells were lysed in NP40 lysis buffer (20 mM Hepes pH 7.5, 150 mM NaCl, 1% Nonidet P 40, 1 mM $Na_3VO_4$) containing EDTA-free complete protease inhibitor cocktail (Boehringer Mannheim Corp., Indianapolis, Ind.), centrifuged at 16,000×g for 10 minutes, and precleared twice with 50 1 of GammaBind G Sepharose slurry (Pharmacia Biotech, Inc., Piscataway, N.J.). MAP kinases were immunoprecipitated with 50 1 GammaBind G Sepharose slurry and 2 μg polyclonal rabbit antibody, specific for the 20 C-terminal residues of p38 α or the 17 C-terminal residues of JNK1 (Santa Cruz Biotechnology, Santa Cruz, Calif.). Immunoprecipitates were washed twice with NP40 lysis buffer and twice with kinase reaction buffer (25 mM HEPES pH 7.5, 10 mM $MgCl_2$, 10 mM $MnCl_2$, 20 mM β-glycerophosphate, 1× EDTA-free complete protease inhibitor cocktail). Kinase reactions were performed for 20 minutes at 30° C. in kinase reaction buffer containing 50 μM ATP and 5 μCi γ-$^{32}$P-ATP (3000 Ci/mmol, Amersham Corp., Arlington Heights, Ill.) with 0.5 μg GST-MAPKAPK2 (Upstate Biotechnology, Lake Placid, N.Y.) as p38 substrate or 2 μg GST-c-JUN (BioMol, King of Prussia, Pa.) as JNK-1 substrate. Samples were boiled in SDS sample buffer, electrophoresed in 10% Tris-Glycine polyacrylamide gels and transferred to PVDF membranes (Novex, San Diego, Calif.). Bands were quantified on a Storm 840 PhosphorImager System (Molecular Dynamics Inc., Sunnyvale, Calif.). Membranes were stained for p38 and JNK1 protein using the p38 and JNK1 antibodies described above and the Vistra ECF Western blotting system (Amersham).

Western Blotting.

Western blot analyses were carried out as described (27). For detection of IRAK and IκB-α protein levels, NP40 cell lysates (1×10$^5$ cells/sample) were separated on SDS-PAGE and transferred to nitrocellulose (MSI, Westboro, Mass.). The filters were immunoblotted with IRAK antiserum (1:1000 dilution) or rabbit antibody to IκB-α (Santa Cruz Biotechnology). The bands corresponding to specific proteins were detected by HRP conjugated rabbit IgG and ECL (Amersham).

NF-κB Mobility Shift Assay.

After stimulation, the cells from 100 mm plates were suspended in 500 μl of Buffer A (10 mM Hepes pH 7.9, 10 mM KCl, 100 μM EDTA, 100 μM EGTA, 1 mM DTT, 500 μM phenylmethylsulfonyl fluoride) and incubated on ice for 15 min. After adding 30 μl of 10% NP40, the samples were centrifuged at 14000 rpm at 4° C. for 30 seconds. The pellet was washed once with buffer A and 50 μl of buffer B (20 mM Hepes pH 7.9, 400 mM NaCl, 1 mM EDTA, 1 mM EGTA, 1 mM DTT, 1 mM phenylmethylsulfonyl fluoride) was added, vortexed and further incubated for 30 minutes at 4° C. Nuclear extracts were obtained by centrifugation of the samples at 14,000 rpm for 10 min. Protein concentrations were measured by the BCA method (Pierce, Rockford, Ill.). The consensus double stranded oligonucleotide for NF-κB binding (Santa Cruz Biotech) was labeled by T4 Polynucleotide kinase. The nuclear binding reaction was carried out with 5 μl of nuclear extract (10 μg), 1 μl of Poly(dI-dC), 1 μof labeled probe (100,000 cpm), 5 μl 4× buffer (20 mM Hepes pH 7.9, 20 mm MgCl$_2$, 1 mM EDTA) and 8 μl of 25% glycerol for 30 minutes at room temperature. The binding complexes were separated on 6% polyacrylamide/0.5× TBE gels and detected by autoradiography.

Northern Blot Analusis and IL-6 ELISA.

For IL-6 mRNA detection, EF cells cultured in 100 mm plates were treated with IL-1β or TNFα for 3 hours at 37° C. Total RNA was extracted from EF cells with RNAzol (Tel-Test, Inc., Friendwood, Tex.). Northern blot analysis was performed as described (28) using a mouse IL-6 cDNA probe prepared by PCR from commercial mouse IL-6 cDNA template and oligonucleotides (Clontech, Palo Alto, Calif.). For detection of secreted IL-6 protein, EF (5×10$^4$/well) and SF (1×10$^4$/well) cells were incubated overnight in flat-bottom microtiter plates in 10% FCS-DMEM. After 2–4 hour incubation with low endotoxin 1% FCS-RPMI-1640 medium (Sigma), cells were treated for 8 hours with mouse IL-1β in fresh medium. Supernatants were then collected and analyzed for IL-6 using commercial ELISA kits (Endogen, Inc., Woburn, Mass. or Genzyme), with recombinant mouse IL-6 as a standard.

IRAK-eficient Cells.

To investigate whether IRAK is indispensable for IL-1 signaling pathway, IRAK deficient mouse primary EF cells were prepared from mouse embryos injected with embryonic stem cells carrying a disrupted IRAK gene as described in Materials and Methods. The IRAK gene was disrupted by deletion of exons 5 to 7, which encode the N-terminal portion of the kinase domain, subdomains I to V, including conserved amino acids involved in ATP binding (FIG. 1A). The deletion was confirmed by Southern hybridization (FIG. 1B). Detection of only the disrupted IRAK allele in male embryonic stem cells suggests that the mouse IRAK gene is located on the X chromosome. Consistent with our finding, the human IRAK gene was also reported to be on the X chromosome (GenBank accession number U52112). The absence of IRAK protein in EF cells containing the disrupted IRAK allele was demonstrated by immunoblotting with an anti-IRAK antiserum (FIG. 1C). The lack of IRAK expression in IRAK-deficient EF cells enabled us to evaluate the importance of IRAK in IL-1 signaling.

Defective Activation of JNK and p38 in IRAK Deficient Cells.

Figure 2A:
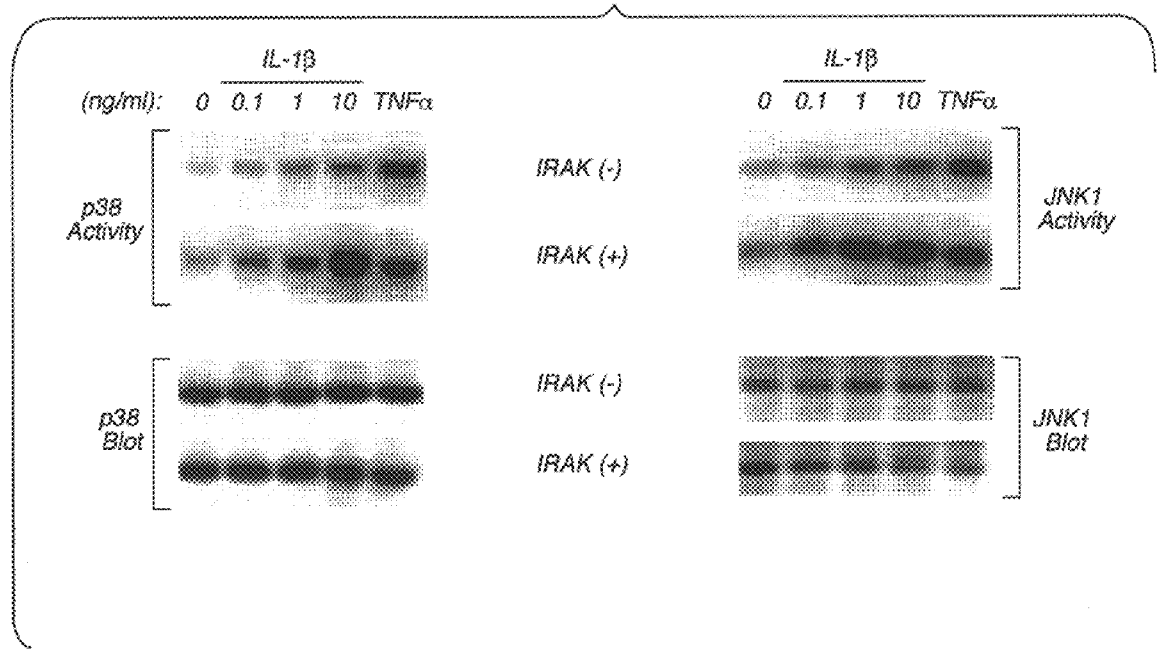
FIG. 2 Panels A–B show defective IL-1-induced p38 and JNK activation in IRAK-deficient EF cells. IRAK-deficient (−) or control (+) EF cells were stimulated with IL-1α (0.1–10 ng/ml) or TNFα (100 ng/ml) for 10 minutes at 37° C., and immune complex kinase assays for p38 and JNK-1 activity were performed. (A) Phosphorylation of MAPKAPK-2 by immunoprecipitated p38, and phosphorylation of c-Jun by immunoprecipitated JNK-1. Western blotting for p38 and JNK1 was performed as a loading control. (B) Quantitation of p38 and JNK-1 activation. p38 and JNK-1 kinase assays were quantitated by Phosphorlmager (Molecular Dynamics), normalized to the amount of p38 or JNK1 detected by Western blotting for each sample, and to the activity in unstimulated IRAK deficient EF cells for each assay. The p38 data are representative of three experiments, and the JNK-1 data are expressed as an average of two experiments.
Figure 2B:
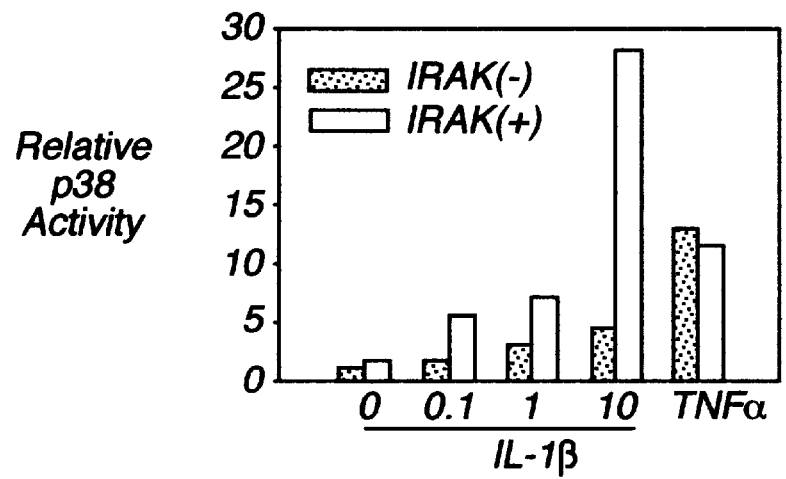
Figure 2B:
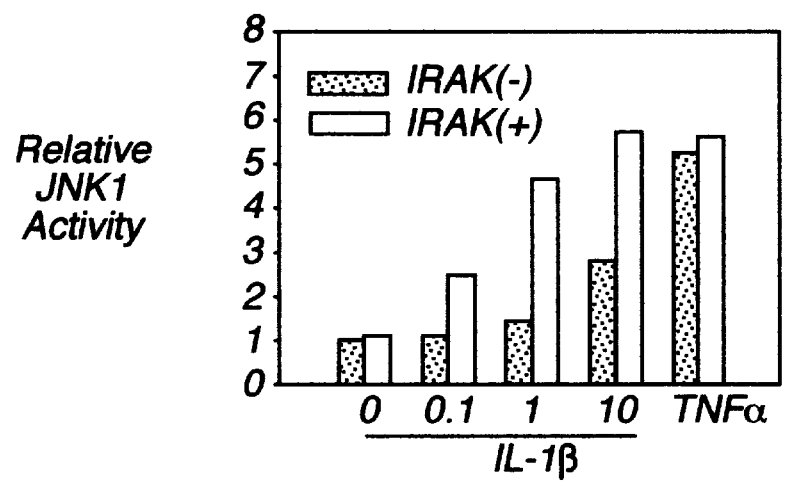

JNK and p38 are strongly activated by IL-1, TNF, cell stress and LPS (29–33). JNK phosphorylates the trans-activation domain of c-Jun which is involved in the activation of AP-1-dependent genes, including genes involved in inflammatory responses (29–31). p38 is also involved in activation of gene expression and protein synthesis 10 during inflammation, including IL-1-induced IL-6 and prostaglandin synthesis (34). The proximal events responsible for IL-1 induced JNK and p38 activation are only partially understood. We therefore compared IL-1-induced activation of JNK and p38 in IRAK-deficient and control EF cells. JNK activity was measured by in vitro kinase assays of JNK immunoprecipitates, using c-Jun as substrate. Activation of JNK was reduced in IRAK-deficient cells by two to three fold at all concentrations of IL-1 tested, although not completely eliminated (FIG. 2). This defect in JNK activation was IL-1 specific, since TNF-α induced JNK activity was comparable in control and IRAK-deficient cells. Activation of p38 was measured in p38 immunoprecipitates using MAPKAPK-2 as a substrate. IL-1-induced activation of p38 was also reduced in IRAK-deficient cells compared to control cells, by three to five fold at all concentrations of IL-1 tested. In contrast, TNF-α induced p38 activity was similar in control and IRAK deficient cells (FIG. 2). These results demonstrate that IL-1-induced JNK and p38 activities are both specifically reduced in IRAK-deficient cells, and implicate IRAK as the most proximal signaling component in the activation of the JNK and p38 pathways.

Defective Activation of NF-B.

Figure 3A:
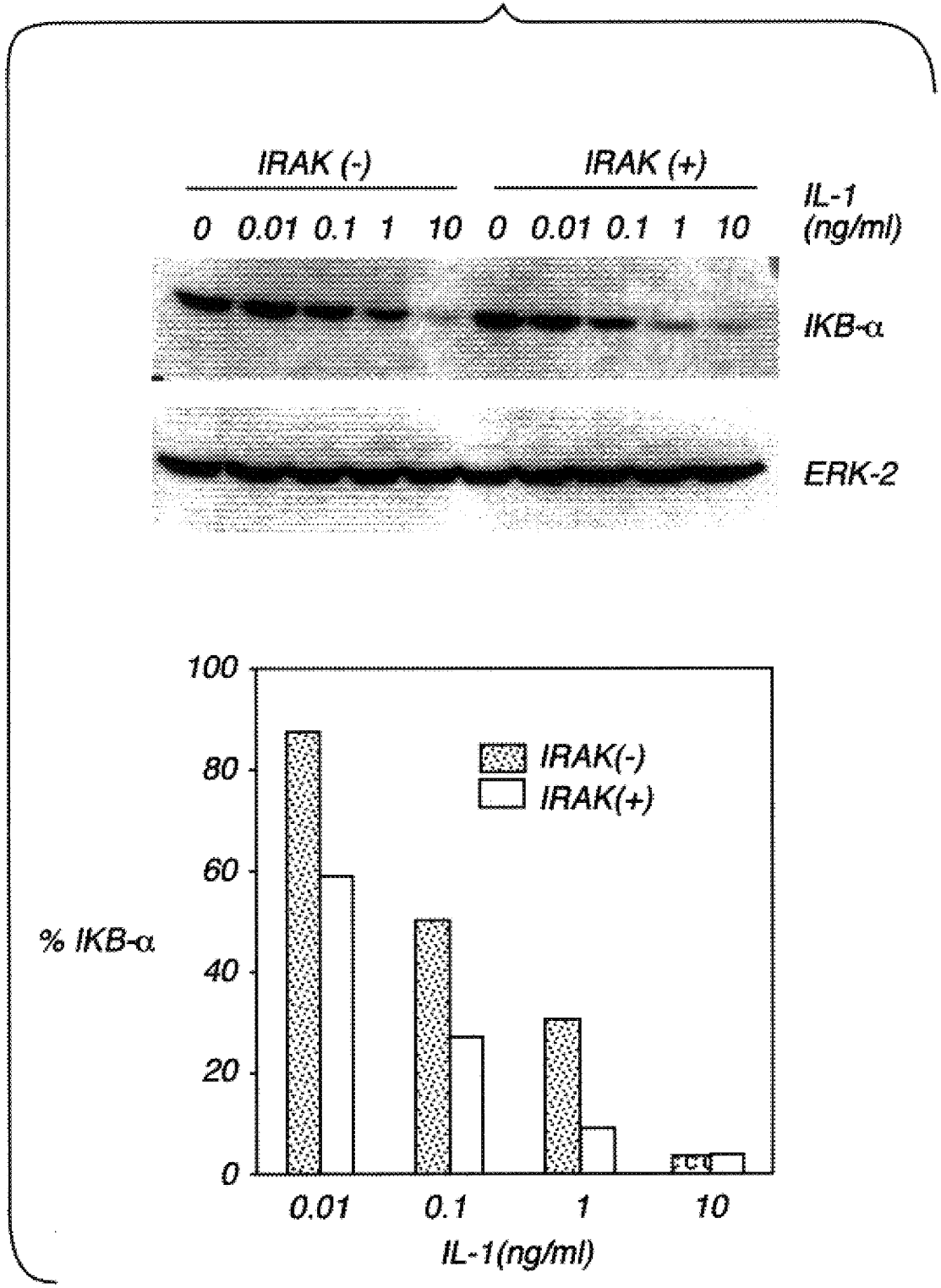
FIG. 3 Panels A–B show reduced activation of the NF-κB pathway by IL-1 in IRAK-deficient cells. (A) Inefficient IκB degradation in IRAK-deficient EF cells. Control (+) and IRAK-deficient (−) cells were stimulated with IL-1 for 15 minutes at 37° C. Proteins in cell lysates were separated on SDS-PAGE and IκB was detected with an IκB-α specific antibody. Equal amounts of sample loading were demonstrated by subsequent blotting of the same filter with an antibody specific to ERK2. The intensity of the protein bands was quantitated by densitometry. The amount of IκB in the IL-1-stimulated cells is expressed as the percentage of that in unstimulated cells. (B) Decreased activation of NF-κB by IL-1 in IRAK-deficient cells. EF cells were stimulated with IL-1 or TNF-α for 30 minutes at 37° C. Nuclear extracts were prepared and NF-κB DNA binding activity was determined with the electrophoretic mobility shift assay. The data are representative of two independent experiments with similar results.
Figure 3B:
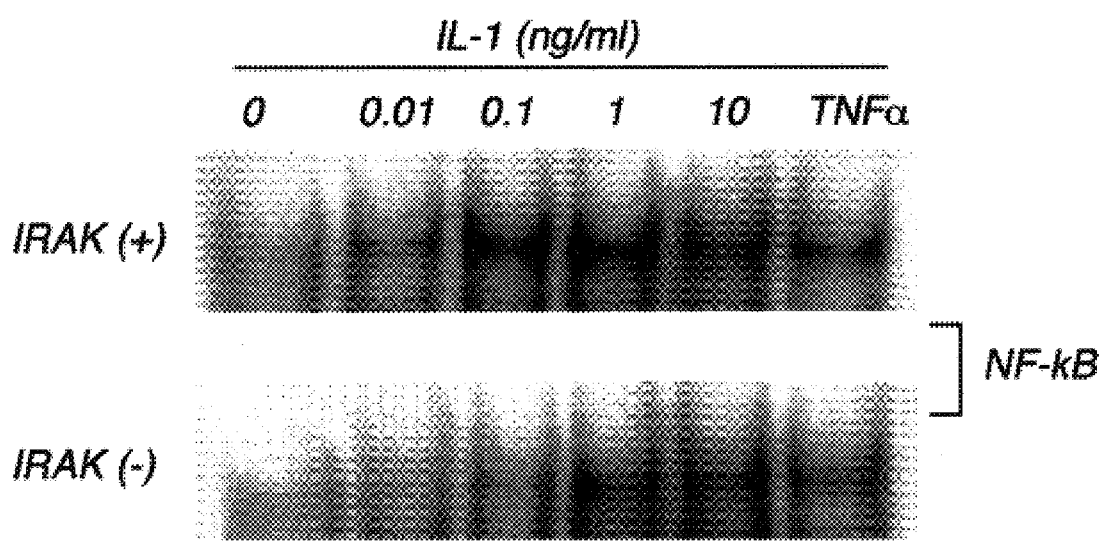

IL-1 and TNFα are the two most efficient activators of the NF-κB family of transcription factors (21, 35). NF-B remains in an inactive state when sequestered by IκB in the cytoplasm. Phosphorylation of IκB by IκB kinases leads to ubiquitination and subsequent degradation of IκB by proteasomes (18–21). Released NF-κB is then translocated to the nucleus where it binds to regulatory sites in NF-κB-induced genes (21). IκB levels in IRAK-deficient and control cells treated with IL-1 were determined by immunoblotting with an IκB-α-specific antibody. At concentrations of IL-1 from 10 pg/ml to 1 ng/ml, IκB degradation was significantly less in IRAK-deficient cells as compared to control cells (FIG. 3A). However, at 10 ng/ml IL-1, IκB-α was degraded almost completely in both IRAK-deficient and control cells. IL-1 induction of the NF-κB pathway was further investigated by examining NF-κB DNA-binding activity in nuclear extracts (FIG. 3B). Significant reduction in NF-κB activation was observed in IRAK-deficient cells at low IL-1 concentrations. Consistent with the results in IκB degradation, NF-κB activation was comparable in control and IRAK-deficient cells at high IL-1 concentrations.

Defective Induction of IL-6.

Figure 4A:
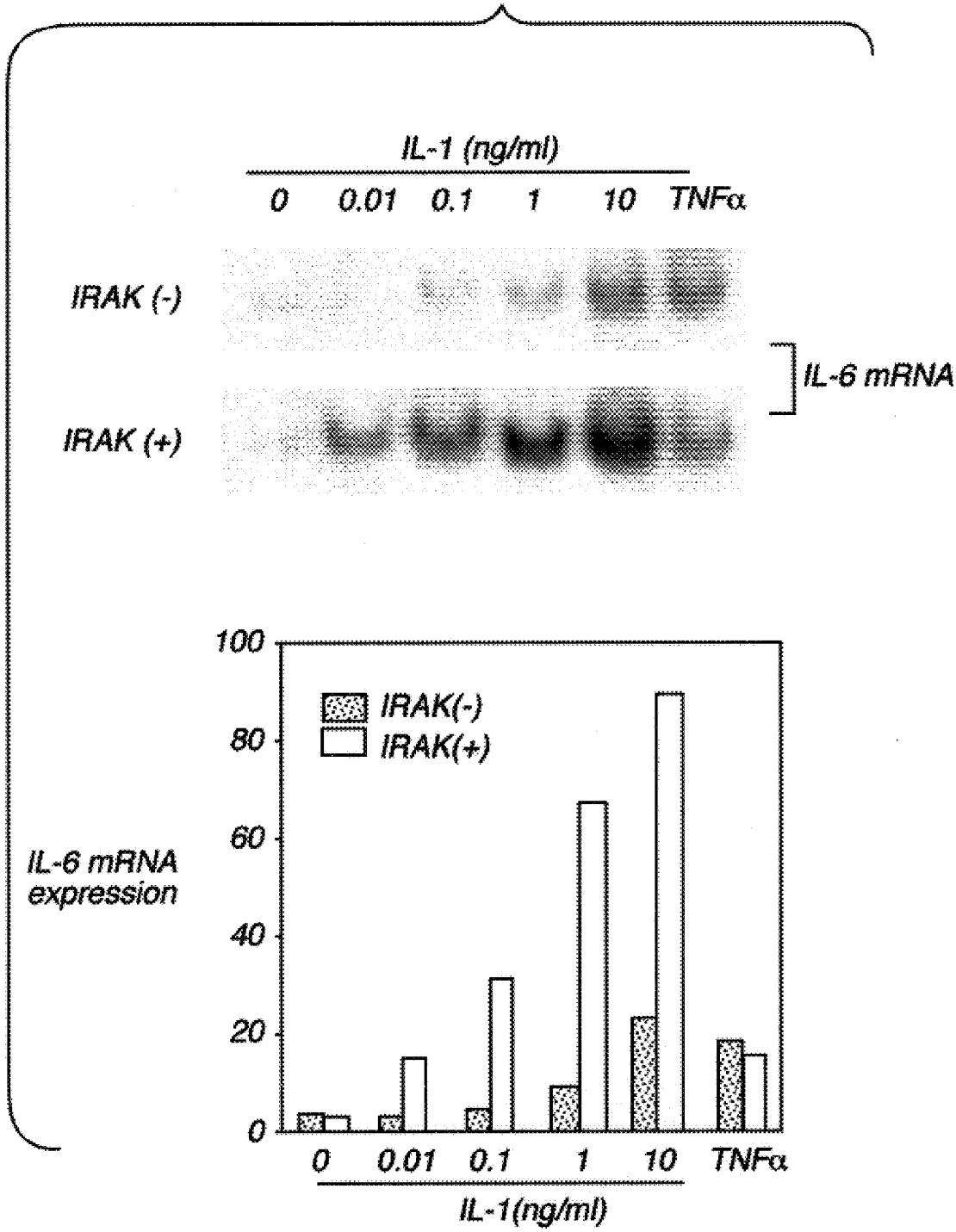
FIG. 4 Panels A–B show decreased induction of IL-6 by IL-1 in IRAK-deficient cells. (A). Decreased induction of IL-6 mRNA in IRAK-deficient cells. Control (+) and IRAK-deficient (−) EF cells were treated with IL-1 or TNFα for 3 hours at 37° C. IL-6 mRNA expression in different samples was detected by Northern hybridization and quantitated on a PhosphorImager. (B). Decreased induction of secreted IL-6 in IRAK-deficient cells. Control (+) and IRAK-deficient (−) EF (top) and SF (bottom) cells were stimulated with IL-1 for 8 hours at 37° C. The amount of secreted IL-6 in culture supernatants was determined by ELISA.
Figure 4B:
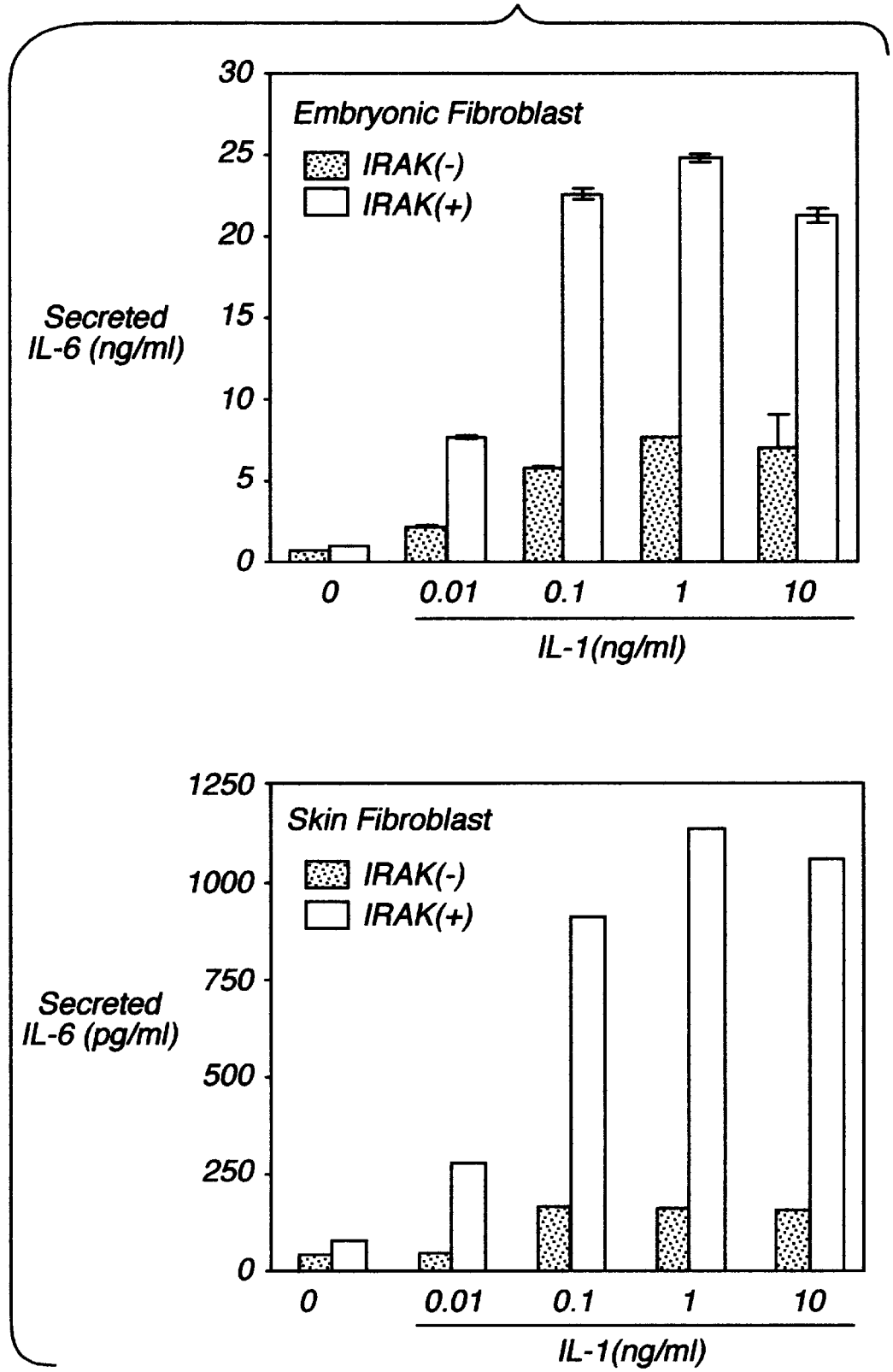

IL-1 signaling triggers cellular responses through the induction of various inflammatory gene products (1). IL-6 is strongly induced by IL-1 via activation of transcription factors including NF-κB and AP-1, which bind to the enhancer elements of the IL-6 gene promoter (6). IL-6 in turn plays a crucial role in inflammation by mediating acute phase reactions (36). To determine whether the observed defects in IL-1 activated signaling results in impaired cellular responses, IL-6 induction in response to IL-1 was measured. Levels of IL-6 mRNA induced by various concentrations of IL-1 were significantly lower in IRAK-deficient EF cells compared to control cells (FIG. 4A). Similar decreases were also found in IL-6 secreted from IRAK-deficient cells compared to control cells (FIG. 4B, top), and at various times after IL-1 treatment. In three independent experiments, IL-6 induction by IL-1 was reduced by 3 to 6 fold. Thus, the reduced IL-1 signaling in IRAK-deficient cells results in decreased IL-6 production. To confirm the defects in IL-1 signaling and cellular response observed in IRAK-deficient EF cells, skin fibroblasts (SF) cells were obtained from mice deficient in IRAK expression, as described in Materials and Methods. Consistent with the observation in EF cells, IL-1-induced IL-6 production was significantly decreased in IRAK-deficient SF cells compared to SF cells prepared from wild type mice (FIG. 4B, bottom). IL-1-induced JNK activation and I B degradation were also found to be defective in IRAK-deficient SF cells.

REFERENCES

1. Dinarello, C. A. 1996. Biologic basis for interleukin-1 in disease. *Blood.* 87: 2095–2147.
2. Glaccum, M. B., K. L. Stocking, K. Charrier, J. L. Smith, C. R. Willis, C. Maliszewski, D. J. Livingston, J. J. Peschon, and P. J. Morrissey. 1997. Phenotypic and functional characterization of mice that lack the type I receptor for IL-1. *J. Immunol.* 159:3364–3371.
3. Labow, M., D. Shuster, M. Zetterstrom, P. Nunes, R. Terry, E. B. Cullinan, T. Bartfai, C. Solorzano, L. L. Moldawer, R. Chizzonite, and K. W. Mcintyre. 1997. Absence of IL-1 signaling and reduced inflammatory response in IL-1 type I receptor-deficient mice. *J. Immunol.* 159:2452–2461.
4. Leon, L. R., C. A. Conn, M. Glaccum, and M. J. Kluger. 1996. IL-1 type I receptor mediates acute phase response to turpentine, but not lipopolysaccharide, in mice. *Am. J. Physiol.* 271:R1668–R1675.
5. Zheng, H., D. Fletcher, W. Kozak, M. Jiang, K. J. Hofmann, C. A. Conn, D. Soszynski, C. Grabiec, M. E. Trumbauer, A. Shaw, M. J. Kostura, K. Stevens, H. Rosen, R. J. North, H. Y. Chen, M. J. Tocci, M. J. Kluger, and L. H. T. Van der Ploeg. 1995. Resistance to fever induction and impaired acute phase response in interleukin-1-deficient mice. *Immunity.* 3:9–19.
6. Bankers-Fulbright, J. L., K. R. Kalli, and D. J. McKean. 1996. Interleukin-1 signal transduction. *Life Sci.* 59:61–83.
7. Wesche, H., C. Korherr, M. Kracht, W. Falk, K. Resch, and M. U. Martin. 1997. The interleukin-1 receptor accessory protein (IL-1 RAcP) is essential for IL-1-induced activation of interleukin-1 receptor-associated kinase (IRAK) and stress-activated protein kinases (SAP kinases). *J. Biol. Chem.*, 272:7727–7731.
8. Korher, C., R. Hofmeister, H. Wesche, and W. Falk, 1997. A critical role for interleukin-1 receptor accessory protein in interleukin-1 signaling. *Eur. J. Immunol.* 27:262-267.
9. Huang, J., X. Gao, S. Li, and Z. Cao. 1997. Recruitment of IRAK to the interleukin 1 receptor complex requires interleukin 1 receptor accessory protein. *Proc. Natl. Acad. Sci. U.S.A.* 94:12829–12832.
10. Muzio, M., J. Ni, P. Feng, and V. M. Dixit. 1997. IRAK (Pelle) family member IRAK2 and MyD88 as proximal mediators of IL-1 signaling. *Science.* 278:1612–1615.
11. Wesche, H., W. J. Henzel, W. Shillinglaw, S. Li, and Z. Cao. 1997. MyD88: An adapter that recruits IRAK to the IL-1 receptor complex. *Immunity.* 7:837–847.
12. Croston, E., Z. Cao, and D. V. Goeddel. 1995. NF-B activation by interleukin-1 (IL-1) requires an IL-1 receptor-associated protein kinase activity. *J. Biol. Chem.* 270:16514–16517.
13. Cao, Z., W. J. Henzel, and X. Gao. 1996. IRAK: A kinase associated with the interleukin-1 receptor. *Science.* 271:1128–1131.
14. Cao,Z., J. Xiong, M. Takeuchi, T. Kurama, and D. V. Goeddel. 1996. TRAF6 is a signal transducer for interleukin-1. *Nature.* 383:443–446.
15. Song, H. Y., C. H. Regnier, C. J. Kirschning, D. V. Goeddel, and M. Rothe. 1997. Tumor necrosis factor (TNF)-mediated kinase cascades: bifurcation of nuclear factor-kB and c-jun N-terminal kinase (JNK/SAPK) pathways at TNF receptor-associated factor 2. *Proc. Natl. Acad. Sci. U.S.A.*, 94:9792–9796.
16. Malinin, N. L., M. P. Boldin, A. V. Kovalenko, and D. Wallach. 1997. MAP3K-related kinase involved in NF-κB induction by TNF, CD95 and IL-1. *Nature.* 385:540–544.
17. Natoli, G., A. Costanzo, F. Moretti, M. Fulco, C. Balsano, and M. Levrero. 1997. Tumor necrosis factor (TNF) receptor 1 signaling downstream of TNF receptor-associated factor 2. Nuclear factor KB (NFKB)-inducing kinase requirement for activation of activating protein 1 and NF.kappa.B but not of c-Jun N-terminal kinase/stress-activated protein kinase. *J. Biol. Chem.*, 272:26079–26082.
18. DiDonato, J. A., M. Hayakawa, D. M. Rothwarf, E. Zandi, and M. Karin. 1997. A cytokine-responsive IκB kinase that activates the transcription factor NF-κB. *Nature.* 388:548–554.
19. Woronicz, D., X. Gao, Z. Cao, M. Rothe, and D. V. Goeddel. 1997. IκB kinase-β: NF-κB activation and complex formation with IκB kinase-β and NIK. *Science.* 278:866–869.
20. Mercurio, F., H. Zhu, B. W. Murray, A. Shevchenko, B. L. Bennett, J. w. Li, D. B. Young, M. Barbosa, M. Mann, A. Manning, and A. Rao. 1997. IKK-1 and IKK-2: cytokine-activated I B kinases essential for NF-κB activation. *Science.* 278,: 860–866.
21. Baldwin, Jr. A. S. 1996. The NF-κB and IκB proteins: New discoveries and insights. *Annu. Rev. Immunol.* 14:649–681.
22. Shelton, C. A., and S. A. Wasserman. 1993. Pelle encodes a protein kinase required to establish dorsoventral polarity in the drosophila embryo. *Cell.* 72:515–525.
23. Lemaitre, B., E. Nicolas, L. Michaut, J.-M. Reichhart, and J. A. Hoffmann. 1996. The dorsoventral regulatory gene cassette spatzle/toll/cactus control the potent antifungal response in drosophila adults. *Cell.* 86:973–983.
24. Belvin., and K. V. Anderson. 1996. A conserved signaling pathway: The Drosophila Toll-Dorsal Pathway. *Annu. Rev. Cell Dev. Biol.* 12:393–416.
25. Trofimova, M., A. B. Sprenkle, M. Green, T. W. Sturgill, M. G. Goebl, and M. A. Harrington. 1996. Developmental and tissue-specific expression of mouse Pelle-like protein kinase. *J. Biol. Chem.* 271:17609–17612.

26. Fung-Leung, W.-P., M. W. Schilham, A. Rahemtulla, T. M. Kudig, M. Vollenweider, J. Potter, W. van Ewijk, and T. W. Mak. 1991. CD8 is needed for development of cytotoxic T cells but not helper T cells. *Cell*. 65:443–449.
27. Kanakaraj, P., B. Duckworth, L. Azzoni, M. Kamoun, L. C. Cantley, and B. Perussia. 1994. Phosphatidylinositol-3 kinase activation induced upon FcγRIIIA-ligand interaction. *J. Exp. Med*. 179:551–5558.
28. Trotta, R., P. Kanakaraj, B. Perussia. 1996. Fc R-dependent mitogen activated protein kinase activation in leukocytes: a common signal transduction event necessary for expression of TNF-α and early activation genes. *J. Exp. Med*. 184, 1027–1035.
29. Su, B., and M. Karin. 1996. Mitogen activated protein kinase cascade and regulation of gene expression. *Curr. Opin. Immunol*. 8:402–411.
30. Pulverer, B. J., J. M. Kyriakis, J. Avruch, E. Nikolakaki, and J. Woodgett. 1991. Phosphorylation of c-jun mediated by MAP kinases. *Nature*. 353:670–674.
31. Westwick, J. K., C. Weitzel, A. Minden, M. Karin and D. A. Brenner. 1994. Tumor necrosis factor-α stimulates AP-1 activity through prolonged activation of the c-Jun kinase. *J. Biol. Chem*. 269:26396–401.
32. Raingeaud, J., S. Gupta, J. S. Rogers, M. Dickens, J. Han, R. J. Ulevitch, and R. J. Davis. 1995. Proinflammatory cytokines and environmental stress cause p38 mitogen-activated protein kinase activation by dual phosphorylation on tyrosine and threonine. *J. Biol. Chem*. 270:7420–7426
33. Bird, T. A., J. M. Kyriakis, L. Tyshler, M. Gayle, A. Milne, and G. D. Virca. 1994. Interleukin-1 activates p54 mitogen-activated protein (MAP) kinase/stress-activated protein kinase by a pathway that is independent of p21ras, Raf-1, and MAP kinase kinase. *J. Biol. Chem*. 269:31836–31844.
34. Ridley, S. H., S. J. Sarsfield, J. C. Lee, H. F. Bigg, T. E. Cawston, D. J. Taylor, D. L. DeWitt, and J. Saklatvala. 1997. Actions of IL-1 are selectively controlled by p38 mitogen-activated protein kinase. Regulation of prostaglandin H synthase-2, metalloproteinases, and IL-6 at different levels. *J. Immunol*. 158:3165–3173.
35. Osborn, L., S. Kunkel, and G. J. Nabel. 1989. Tumor necrosis factor .alpha. and interleukin 1 stimulate the human immunodeficiency virus enhancer by activation of the nuclear factor .kappa.B. *Proc. Natl. Acad. Sci. U.S.A*. 86:2336–2340.
36. Akira, S., and T. Kishimoto. 1992. IL-6 and NF-IL-6 in acute-phase response and viral infection. *Immunol. Rev*. 127:25–50.
37. Berghe, W. V., S. Plaisance, E. Boone, K. De Bosscher, M. L. Scmitz, W. Fiers, and G. Haegeman. 1998. p38 and extracellular signal regulated kinase mitogen-activated protein kinase pathways are required for nuclear factor-KB p65 transactivation mediated by tumor necrosis factor *J. Biol Chem*. 273:3285–3290.

What is claimed is:

1. A transgenic mouse whose somatic and germ cells comprise a disruption in an endogenous IRAK gene, wherein disruption is generated by targeted replacement with a non-functional IRAK gene, and wherein said disruption results in IRAK-deficient cells from said mouse having a decrease in activation of JNK, activation of p38 and induction of IL-6 in response to IL-1 as compared to wild-type IRAK mice.

2. The mouse of claim 1, wherein said mouse is fertile and transmits the non-functional IRAK gene to its offspring.

3. The mouse of claim 1, wherein the non-functional IRAK gene has been introduced into an ancestor of the mouse at an embryonic stage by microinjection of altered embryonic stem cells into mouse blastocysts.

4. An isolated cell line derived from the transgenic mouse of claim 1.

5. A method for producing a transgenic mouse whose somatic and germ cells comprise a disruption in an endogenous IRAK gene, wherein said disruption is generated by targeted replacement with a non-functional IRAK gene, said method comprising:
    (a) introducing an IRAK gene targeting construct comprising a selectable marker sequence into a mouse embryonic stem cell;
    (b) introducing said mouse embryonic stem cell into a mouse blastocyst;
    (c) transplanting said blastocyst into a recipient mouse;
    (d) allowing said blastocyst to develop to term;
    (e) identifying a transgenic mouse whose genome comprises a disruption of an endogenous IRAK gene in at least one allele; and
    (f) breeding the mouse of step (e) to obtain a transgenic mouse whose genome comprises a homozygous disruption of the endogenous IRAK gene, wherein said disruption results in IRAK-deficient cells and said mouse having a decrease in activation of JNK, activation of p38 and induction of IL-6 in response to IL-1 as compared to wild-type IRAK mice.

6. The method of claim 5 wherein the introducing of step (a) is by electroporation, or microinjection.

* * * * *